United States Patent [19]

Mitra

[11] Patent Number: 4,648,843

[45] Date of Patent: Mar. 10, 1987

[54] METHOD OF DENTAL TREATMENT USING POLY(ETHYLENICALLY UNSATURATED) CARBAMOYL ISOCYANURATES AND DENTAL MATERIALS MADE THEREWITH

[75] Inventor: Sumita B. Mitra, Woodbury, Minn.

[73] Assignee: Minnesota Mining and Manufacturing Company, St. Paul, Minn.

[21] Appl. No.: 757,124

[22] Filed: Jul. 19, 1985

[51] Int. Cl.$^4$ .................... C09K 3/00; A61L 8/00; A61K 5/01

[52] U.S. Cl. .................... 433/201.1; 106/35; 433/217.1; 433/228.1; 523/120

[58] Field of Search .................... 523/120; 544/222; 106/35; 526/301, 261; 528/55; 433/201.1, 217.1, 228.1; 106/35

[56] References Cited

U.S. PATENT DOCUMENTS

| | | | |
|---|---|---|---|
| 3,066,112 | 11/1962 | Bowen | 260/41 |
| 3,251,818 | 5/1966 | Juenge et al. | 260/88.3 |
| 3,480,627 | 11/1969 | Heinert | 260/248 |
| 3,825,518 | 7/1974 | Foster et al. | 260/42.52 |
| 4,110,184 | 8/1978 | Dart et al. | 204/159.23 |
| 4,128,537 | 12/1978 | Markiewitz | 528/49 |
| 4,145,544 | 3/1979 | Kuehn | 544/222 |
| 4,159,376 | 6/1979 | Kuehn | 544/222 |
| 4,195,146 | 3/1980 | Markiewitz et al. | 526/261 |
| 4,407,984 | 10/1983 | Ratcliffe et al. | 523/115 |
| 4,485,226 | 11/1984 | Noll et al. | 528/45 |
| 4,503,169 | 3/1985 | Randklev | 523/117 |

FOREIGN PATENT DOCUMENTS

| | | |
|---|---|---|
| 1226298 | 3/1971 | United Kingdom . |
| 12784113 | 6/1972 | United Kingdom . |

OTHER PUBLICATIONS

"High Solids Two-Component Polyurethane Coatings", by M. Bock and W. Verdingen, from vol. 43, Organic Coatings and Plastic Chemistry (American Chemical Society, 1980).

U.S. application Ser. No. 629,353 (Hegel).

U.S. application Ser. No. 763,331 (Boettcher et al.).

*Primary Examiner*—Theodore Morris
*Attorney, Agent, or Firm*—Donald M. Sell; James A. Smith; Philip M. Goldman

[57] ABSTRACT

A method for dental treatment using polymerizable carbamoyl isocyanurates in filled or unfilled dental materials such as restoratives, prostheses and sealants, dental materials containing such polymerizable carbamoyl isocyanurates disposed adjacent to teeth, and teeth treated with such dental materials.

16 Claims, No Drawings

METHOD OF DENTAL TREATMENT USING POLY(ETHYLENICALLY UNSATURATED) CARBAMOYL ISOCYANURATES AND DENTAL MATERIALS MADE THEREWITH

TECHNICAL FIELD

This invention relates to a method for the treatment of teeth using filled or unfilled dental materials such as restoratives, prostheses and sealants. This invention also relates to dental materials which can be used for such treatment.

BACKGROUND ART

A variety of references have described polymerizable compounds for use as binders or resins in dental materials. Among commercially available filled dental materials the most widely used are composites based on diglycidylmethacrylate of Bisphenol A (frequently referred to as "Bis-GMA") in combination with a diluent monomer such as triethyleneglycol dimethacrylate. Examples of such composites can be found in, e.g., U.S. Pat. No. 3,066,112.

Also used in dentistry are composites based on polymerizable urethane diacrylates or dimethacrylates such as those described in U.S. Pat. No. 3,825,518, or polymerizable prepolymers formed by the reaction of a urethane prepolymer with an ethylenically unsaturated monomer as described, e.g., in U.S. Pat. No. 4,110,184.

U.S. Pat. No. 4,407,984 contains an isolated reference to, but no examples of, "vinyl isocyanurates" in a list of "vinyl urethanes" which can be used in polymerizable dental compositions. However, the preparation of vinyl isocyanurates can be dangerous and difficult to accomplish.

SUMMARY OF THE INVENTION

The present invention provides a method for treating a tooth which comprises disposing adjacent to said tooth a dental material comprising a polymerized or unpolymerized poly(ethylenically unsaturated)carbamoyl isocyanurate. For brevity, said poly(ethylenically unsaturated)carbamoyl isocyanurates sometimes will be referred to herein as "polymerizable carbamoyl isocyanurates". The polymerizable carbamoyl isocyanurate can be polymerized (i.e., cured) after it is disposed adjacent to the tooth, as in the case of a restorative or sealant, or before it is disposed adjacent to the tooth, as in the case of a prosthesis. The present invention also provides dental materials comprising said polymerizable carbamoyl isocyanurates, said dental materials being disposed adjacent to a tooth. The ingredients of the dental materials used in this invention have refractive indices which enable close approximation of the appearance of natural dentition. When filled with inorganic or organic fillers, the dental materials used in this invention can have very high diametral tensile and compressive strengths, thus permitting their use in demanding applications within the mouth.

DETAILED DESCRIPTION

The method of the present invention employs filled or unfilled dental materials such as direct esthetic restorative materials (e.g., anterior and posterior restoratives), prostheses, sealants, veneers, cavity liners, orthodontic bracket adhesives, crown and bridge cements, artificial crowns, artificial teeth, dentures, and the like. These dental materials are used in the mouth and are disposed adjacent to natural teeth. The phrase "disposed adjacent to" as used herein will refer to the placing of a dental material in temporary or permanent bonded (e.g., adhesive) or touching (e.g., occlusal or proximal) contact with a natural tooth. The term "composite" as used herein will refer to a filled dental material. The term "restorative" as used herein will refer to a composite which is polymerized after it is disposed adjacent to a tooth. The term "prosthesis" as used herein will refer to a composite which is shaped and polymerized for its final use (e.g., as a crown, bridge, veneer, inlay, onlay or the like) before it is disposed adjacent to a tooth. The term "sealant" as used herein will refer to a lightly filled composite or to an unfilled dental material which is cured after it is disposed adjacent to a tooth. "Polymerizable", as used herein, refers to curing or hardening the dental material, e.g., by free-radical, ionic or mixed reaction mechanisms.

The polymerizable carbamoyl isocyanurates used in this invention are poly(ethylenically unsaturated) carbamoyl esters, thioesters or amides of isocyanuric acid. They contain an isocyanuric acid ring, one or more radicals containing carbamoyl groups (e.g. carbamate, carbamoyl thioester or urea groups having the respective formulas —NHC(O)O—, —NHC(O)S— or —NHC(O)NH—), and two or more polymerizable ethylenically unsaturated groups. Preferably the isocyanuric acid ring is joined at at least one of its nitrogen atoms, by at least one of said radicals, to at least one of said ethylenically unsaturated groups, with the remainder of said ethylenically unsaturated groups being joined to the same or another of said radicals, or to another nitrogen atom of said ring.

Preferred polymerizable carbamoyl isocyanurates contain a trivalent isocyanuric acid ring of the formula:

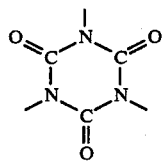

I joined at at least one of its nitrogen atoms to at least one radical containing a carbamoyl group of the formula:

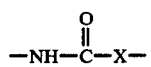

II where X is O, S or NH. Preferably X is O.

A preferred subclass of polymerizable carbamoyl isocyanurates used in this invention has the formula:

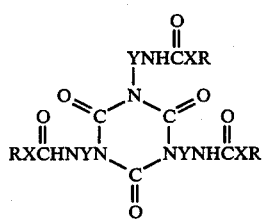

III where each X independently is as defined above, each Y independently is a non-interfering polyvalent (e.g., divalent) organic linking group, e.g., an alkylene, oxyalkylene, cycloalkylene, arylene or aralkylene group which can contain non-interfering heteroatoms such as O, N, S, P, and the like or non-interfering substituents such as halo (e.g., Cl—) and the like, and where each R independently is an organic group with the proviso that at least two polymerizable ethylenically unsaturated groups are present within the R groups as a whole. The term "non-interfering" as used herein will refer to groups, heteroatoms, or substituents which do not prevent the polymerizable carbamoyl isocyanurate from being used safely and efficaciously in the mouth.

Examples of the linking group Y include, but are not limited to:

—$(CH_2)_n$— where n = 1 to 10,

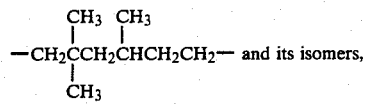

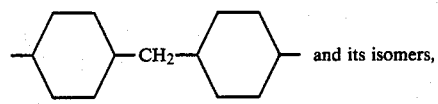

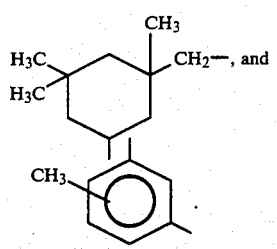

Aliphatic and cycloaliphatic Y groups are preferred, and hexamethylene and isophorone Y groups are especially preferred.

Preferably, the R groups as a whole contain two or more polymerizable ethylenically unsaturated groups of the formula:

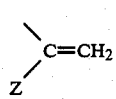           IV where Z is hydrogen, halogen, or lower alkyl (e.g., methyl, ethyl, n-propyl or isoproyl). Preferably Z is hydrogen or methyl.

Groups of Formula IV can be connected to one another within a single R group or can be connected to the remainder of the polymerizable carbamoyl isocyanurate directly or through suitable polyvalent (e.g., divalent) linking groups. Suitable linking groups include alkylene, oxyalkylene, cycloalkylene, arylene or aralkylene radicals.

Preferably the R groups are independently selected from the group consisting of alkylmono- or alkylpoly(acrylates and methacrylates), and mixtures thereof. Examples of suitable R groups include, but are not limited to:

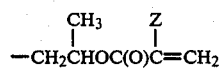

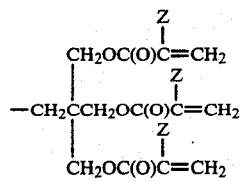

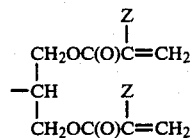

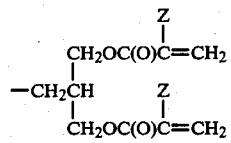

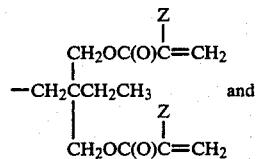

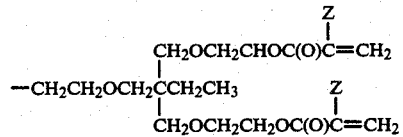

where Z is as defined above.

Use of acrylate-containing R groups tends to reduce the viscosity of the polymerizable carbamoyl isocyanurate. However, use of methacrylate-containing R groups tends to improve pulpal compatibility, especially if the cured dental material has a low degree of polymerization. A judicious use of both of these types of R groups may be desired to obtain an optimum balance of viscosity and pulpal response.

Compounds of the preferred subclass of Formula III can be prepared using a variety of synthetic routes shown below and in U.S. Pat. Nos. 4,128,537, 4,485,226, 4,503,169 and (copending U.S. application Ser. No. 629,353, filed July 10, 1984), the disclosures of which are incorporated herein by reference. It is convenient to derive such compounds from reactions between triisocyanato isocyanurates of the formula:

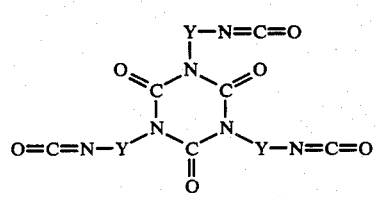           V where Y is as defined above, and mono- or poly(ethylenically unsaturated) compounds containing isocyanate reactive groups, e.g., hydroxy-, thio- or aminoalkyl mono-or poly(acrylates and methacrylates).

The triisocyanato isocyanurates of Formula V can be formed by trimerizing a precursor diisocyanate of the formula:

$$Y(NCO)_2 \qquad \qquad VI$$

in which case the Y group of the precursor diisocyanate VI and the product triisocyanato isocyanurate V will be the same, unless modified after trimerization. For example, when hexamethylene diisocyanate is trimerized, the resultant Y groups will each be hexamethylene radicals, i.e., $-(CH_2)_6-$.

Commercially available triisocyanato isocyanurates of Formula V include "T-1890", a trimerized isophorone diisocyanate available from Chemische Werke Huls Aktiengesellschaft, Germany, and "Desmodur N3300", a tris(6-isocyanato hexamethylene) isocyanurate available from Mobay Chemical Corp., Pittsburgh.

Isocyanate reactive compounds suitable for preparing dental materials containing preferred R groups are available commercially or can be synthesized by methods known in the art. See e.g., U.S. Pat. Nos. 4,128,537 and 4,485,226.

Using IUPAC nomenclature, compounds within the preferred subclass of Formula III can have lengthy names. For simplicity, acrylate- or methacrylate-containing R groups will be represented with the symbols "A" or "MA", respectively. A superscript will denote the number of ethylenically unsaturated sites within individual R groups, and subscripts will denote the number of such R groups within the polymerizable carbamoyl isocyanurate. "HMDIT" will refer to isocyanurates derived from the trimer of hexamethylene diisocyanate, and "IPDIT" will refer to isocyanurates derived from the trimer of isophorone diisocyanate. Hence, in HMDIT, Y will be $-(CH_2)_6-$ and in IPDIT, Y will be an isophorone ring. "TDIT" will refer to isocyanurates derived from the trimer of toluene diisocyanate.

Using the above nomenclature, $HMDIT(MA^1)_2(A^3)_1$ denotes a polymerizable carbamoyl isocyanurate derived from the trimer of hexamethylene diisocyanate, and containing two monomethacrylated R groups and one triacrylated R group. A variety of compounds fall within such description depending, for example, on the alkyl groups present in the R groups. The structure of one such compound is set forth below in Formula XI. The IUPAC nomenclature for the compound of Formula XI is 1,3-[[(2-(1-oxo-2-methyl-2-propenyl)oxy)ethyloxycarbonylamino]hexyl]-5-[[2,2-bis[((1-oxo-2-propenyl)oxy)methyl]-3-((1-oxo-2-propenyl)oxy)-propyloxycarbonylamino]hexyl]-1,3,5,-triazine-2,4,6-(1H,3H,5H)trione.

Table I shows some of the polymerizable carbamoyl isocyanurates that can be used in this invention.

TABLE I

| COMPOUND | NOTATION | FORMULA | REFERENCE |
|---|---|---|---|
| 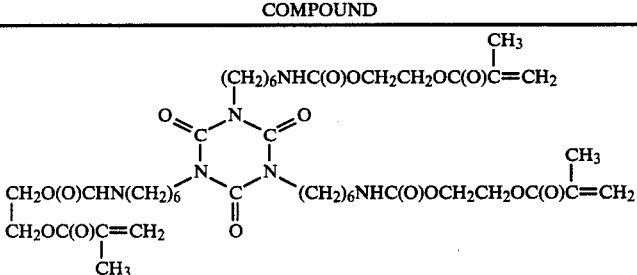 | $HMDIT(MA^1)_3$ | VII | Example 1 |
| 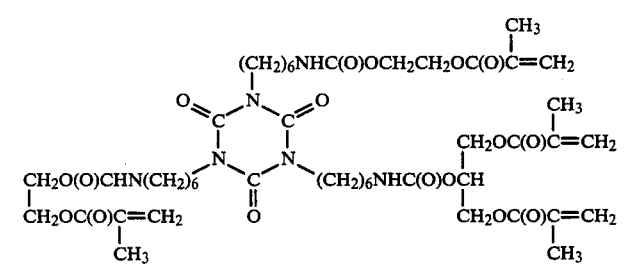 | $HMDIT(MA^1)_2(MA^2)_1$ | VIII | — |
| 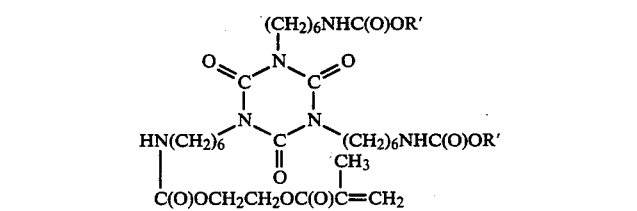 where R' is a mixture of 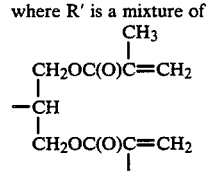 | $HMDIT(MA^1)_1(MA^2)_2$ 80% | IX | Example 2 |

TABLE I-continued

| COMPOUND | NOTATION | FORMULA | REFERENCE |
|---|---|---|---|
| and $-CH_2CHOC(O)\underset{CH_3}{C}=CH_2$ $\phantom{-CH_2CH}CH_2OC(O)\underset{CH_3}{C}=CH_2$ | 20% | | |
| [triazine trione with three $(CH_2)_6NHC(O)OR'$ substituents] where R' is as defined above | HMDIT(MA$^2$)$_3$ | X | — |
| [triazine trione structure] | HMDIT(MA$^1$)$_2$(A$^3$)$_1$ | XI | Example 3 |
| [triazine trione structure] | HMDIT(MA$^1$)$_2$(MA$^3$)$_1$ | XII | Example 4 |
| [triazine trione structure] | HMDIT(MA$^1$)$_1$(A$^3$)$_2$ | XIII | Example 5 |
| [triazine trione structure] | HMDIT(A$^3$)$_3$ | XIV | Example 6 (see also Example 2 of U.S. Ser. No. 629,353) |

TABLE I-continued

| COMPOUND | NOTATION | FORMULA | REFERENCE |
|---|---|---|---|
| 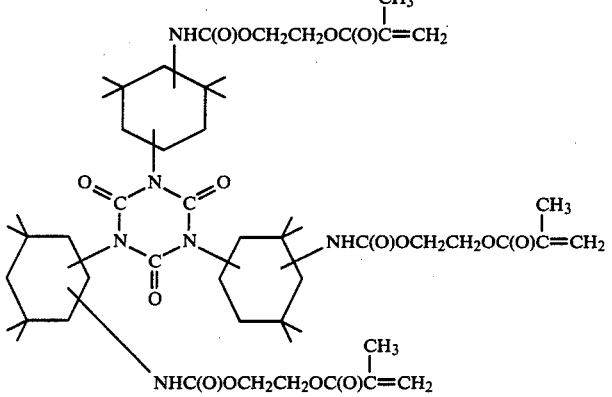 | IPDIT(MA$^1$)$_3$ | XV | Example 7 |
| 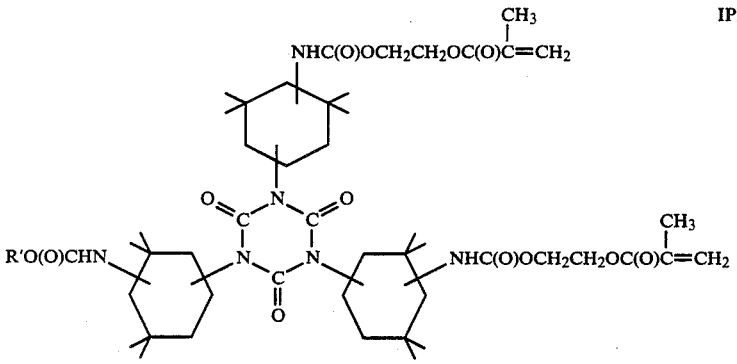 where R' is as defined above | IPDIT(MA$^1$)$_2$(MA$^2$)$_1$ | XVI | Example 8 |
| 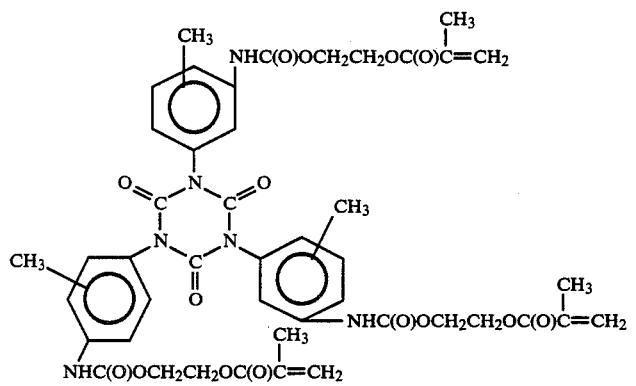 | TDIT(MA$^1$)$_3$ | XVII | Example 9 |

Compounds of Formulas IX, XII, XV and XVI are preferred.

In addition, copolymerizable diluent monomers are preferably used in admixture with the above polymerizable carbamoyl isocyanurates to modify their viscosity and/or refractive index and facilitate the addition of fillers to form composites. The term "copolymerizable" refers to the ability of the diluent monomer to compatibly cure with the polymerizable carbamoyl isocyanurates used in the invention. These diluent monomers are typically mono- or polyacrylates or methacrylates of low viscosity, e.g., 1–500 cps. A judicious choice of the type and amount of diluent monomer assists in the adjustment of the refractive index of the resulting mixture and also facilitates the mixing of the composite.

Examples of suitable diluent monomers include, but are not limited to, diethylene glycol diacrylate, 1,3-butylene glycol diacrylate, 2,2-dimethylpropane 1,3-diacrylate, ethylene glycol dimethacrylate, diethylene glycol dimethacrylate, tetraethylene glycol dimethacrylate, polyethylene glycol 200 dimethacrylate, 1,6-hexanediol dimethacrylate and "Chemlink 2000" (an oligomer of a $C_{12}$ hydrocarbon diol), all commercially available from Sartomer Company, West Chester, Pa.

Preferred diluent monomers are those which provide an optimal balance of such factors as water absorption, strength, rate of cross-linking, toxicity or irritancy and shrinkage. Examples of preferred diluent monomers are triethyleneglycol dimethacrylate ("TEGDMA") and ethoxylated bisphenol A dimethacrylate ("EBDMA"), both available from Sartomer Co.

Filler particles suitable for use in the composites of the present invention are well known in the art and are generally organic or inorganic fillers which are suitable for use in the oral environment. In addition, the filler can be an inorganic-filled organic filler, e.g., as described in U.K. Patent Specification No. 1,278,413.

The filler particles can be radiopaque or non radiopaque. Examples of suitable inorganic fillers are powdered glass, powdered quartz, nitrides (e.g., silicon nitride), borosilicate glass, barium glass, hydroxyapatite, ceramic metal oxides (e.g., $CeO_2$, $Sb_2O_5$, $SnO_2$, $ZrO_2$, SrO, BaO, $Al_2O_3$ and $CaCO_3$), and submicron silica particles (e.g., pyrogenic silicas such as the "Aerosil" Series "OX 50", "130", "150" and "200" silicas sold by Degussa and "Cab-O-Sil M5" silica sold by Cabot Corp). Examples of suitable organic filler particles include filled or unfilled pulverized acrylates or methacrylates (e.g., polymethyl methacrylate), polycarbonates, polyepoxides, and the like. Preferred filler particles are quartz, submicron silica, and non-vitreous microparticles of the type described in U.S. Pat. No. 4,503,169.

The choice of filler affects important properties of the composite such as its appearance and radiopacity. Appearance is affected in part by adjustment of the amounts and relative refractive indicies of the ingredients of the composite, thereby allowing alteration of the translucence, opacity or pearlescence of the composite. Polymerizable carbamoyl isocyanurates of the invention, either alone or in admixture with diluent monomer, can be prepared with refractive indicies which approach or approximate the refractive indicies of fillers such as quartz (refractive index 1.55), submicron silica (1.46), and 5.5:1 mole ratio $SiO_2:ZrO_2$ non-vitreous microparticles (1.54). In this way the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a filling remains sound. Under other circumstances a non-radiopaque composite may be desirable. For instance, it may be desirable to employ a non-radiopaque composite in order to prepare a crown. In this way the underlying tooth structure will remain discernable by x-ray examination.

It is preferable to treat the surface of the filler particles with a coupling agent in order to enhance the bond between the filler and the resin. The use of such coupling agents is well known in the art. Examples of suitable coupling agents include gamma-methacryloxypropyltrimethoxy silane, gamma-mercaptopropyltriethoxy silane, gamma-aminopropyltrimethoxy silane, and the like.

The amount of filler which is incorporated into the composite (referred to herein as the "loading level" and expressed as a weight percent based on the total weight of the dental material) will vary depending on the type of filler, the polymerizable carbamoyl isocyanurate and diluent monomer, and the end use of the composite. Compressive strength and diametral tensile strength generally increase with higher loading levels. In general, the loading levels which can be achieved with any particular filler material are higher with the preferred polymerizable carbamoyl isocyanurates of the invention than those which can be achieved with conventional dental resins.

For some dental materials (e.g., sealants), the polymerizable carbamoyl isocyanurates can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications such as veneers, cavity liners and orthodontic bracket adhesives the loading levels will generally be less than about 60 weight percent, while in applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Preferably, the composites used in this invention contain a bimodal or polymodal mixture of fillers including a submicron silica filler (such as "Aerosil OX 50") at a preferred submicron silica level of about 5 to 50 weight %, based on the total weight of filler material.

The dental materials of the present invention can be thermally, chemically or photolytically curable. They can contain chemical polymerization initiation systems such as peroxide compounds alone or in combination with suitable amines, sulfur compounds, phosphorus compounds or other chemical compounds capable of reacting with the peroxide to generate free radical species. Alternatively, the dental materials of the present invention can contain light-induced polymerization initiation systems such as ketone or alpha-diketone compounds alone or in combination with suitable amines, peroxides, sulfur compounds, phosphorous compounds, or other chemical compounds capable of reacting with or being sensitized by the ketone or alpha-diketone compounds to effect polymerization of the dental material. Optionally the dental materials of the present invention can be cured outside the mouth without the use of a polymerization initiator, e.g., by the use of electron beam energy, or by the use of thermal energy while the dental material is kept under vacuum or in an inert atmosphere.

The dental materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as a dentin or enamel adhesive by methods known to those skilled in the art.

The following examples are given to illustrate, but not limit, the scope of this invention. Unless otherwise indicated, all parts and percentages are by weight.

EXAMPLE 1

Synthesis of HMDIT (MA$^1$)$_3$ (Formula VII)

0.63 Parts of Irganox 1010 antioxidant (Ciba-Geigy Co.) and 0.05 parts of dibutyltin dilaurate were dissolved in 273 parts of 2-hydroxyothylmethacrylate ("HEMA"). The resulting solution was added dropwise with stirring to 437 parts of the isocyanurate of hexamethylene diisocyanate haYing an isocyanate number of 192 (Desmodur N3300, Mobay) in a reaction vessel equipped with a stirrer, thermometer and addition funnel while keeping the reaction temperature below 70° C. After stirring for 110 minutes the reaction mixture was left to stand at room temperature overnight, at which time no residual isocyanate could be detected by IR spectroscopy.

EXAMPLE 2

Synthesis of HMDIT(MA$^1$)$_1$(MA$^2$)$_2$ (Formula IX)

To 576 parts of the isocyanurate of hexamethylene diisocyanate in a reaction vessel equipped with an air driven stirrer assembly, thermometer and addition funnel were added 0.9 parts of dibutyltin dilaurate and 0.1 parts butylated hydroxytoluene ("BHT"). Stirring was started and 131 parts of HEMA were added in a dropwise fashion so that the reaction temperature remained below 60° C. After the addition of HEMA was complete the reaction mixture was allowed to stir at 60°-70° C. for two hours. This was followed by the addition of 250 parts of TEGDMA in one portion. To the reaction mixture 456 parts of glyceryl dimethacrylate ("GDMA", a mixture of 80% 1,3- and 20% of 1,2-dimethacrylate) were added dropwise so as to keep the reaction temperature below 60° C. When the addition was complete the mixture was stirred at 70° C. for about eight hours until infrared spectroscopy showed that no residual isocyanate peak was present. The product exhibited IR peaks at 1535, 1630, 1710 and 3350 cm$^{-1}$. The HMDIT(MA$^1$)$_1$(MA$^2$)$_2$ resin was a colorless syrupy liquid having a pungent odor. It was soluble in alcohol, chloroform, methylene chloride, tetrahydrofuran and acetone. The resulting resin contained 17.69% TEGDMA by weight.

EXAMPLE 3

Synthesis of HMDIT(MA$^1$)$_2$(A$^3$)$_1$ (Formula XI)

0.6 Parts of Irganox 1010 and 0.9 parts of dibutyltin dilaurate were dissolved in 260 parts of HEMA with slight warming at 40° C. The resulting solution was added dropwise with stirring to 648 parts of the isocyanurate of hexamethylene diisocyanate while keeping the reaction temperature below 60° C. After the addition of HEMA was complete stirring was continued for another hour at 60°-70° C. This was followed by the dropwise addition of 29.8 parts of pentaerythrytol triacrylate ("PETA") so that the reaction temperature remained at 60°-70° C. Heating and stirring were continued for about ten hours at this temperature until no residual isocyanate could be detected by IR spectroscopy. The product exhibited IR peaks at 1535, 1630, 1710 and 3350 cm$^{-1}$.

EXAMPLE 4

Synthesis of HMDIT(MA$^1$)$_2$(MA$^3$)$_1$ (Formula XII)

To 230.4 parts of the isocyanurate of hexamethylene diisocyanate were added 0.196 parts of BHT and 0.9 parts of dibutyltin dilaurate. Stirring was started and 104.8 parts of HEMA were added in a dropwise fashion so that the reaction temperature remained below 65° C. The total time required for addition was about 1.5 hours. The reaction mixture was then allowed to stir at 65° C. for a further 1.5 hour period. This was followed by the dropwise addition of 179.2 parts of pentaerythrytol trimethacrylate ("PETMA") with a hydroxyl equivalent weight of 448, while maintaining the reaction temperature at 60°-65° C. When the addition of PETMA was complete 129 parts of TEDGMA were added and stirring was continued at 60°-65° C. for 12 hours. Infrared spectroscopy showed that no residual isocyanate peak was present at the end of this period and showed peaks indicative of the desired product at 1535, 1630, 1710, and 3350 cm$^{-1}$. The resulting HMDIT(MA$^1$)$_2$(MA$^3$)$_1$ resin was a colorless syrupy liquid which had a pungent odor and was thixotropic in nature. The resin contained 20% TEGDMA by weight.

EXAMPLE 5

Synthesis of HMDIT(MA$^1$)$_1$(A$^3$)$_2$ (Formula XIII)

Irganox 1010 antioxidant (3.0 parts) and dibutyltin dilaurate (0.08 parts) were dissolved in 230 parts HEMA. The resulting solution was added dropwise with stirring to 1093 parts of the isocyanurate of hexamethylene diisocyanate over a 20 minute period. After stirring for an additional 30 minutes, 1553 parts of pentaerythritol triacrylate was added over a 30 minute period, and the mixture was stirred for an additional 30 minutes. The mixture was allowed to stand at room temperature for an additional three day period, at which time no residual isocyanate could be detected by IR spectroscopy. The viscosity of the resultant product was determined to be approximately 130,000 cps.

EXAMPLE 6

Synthesis of HMDIT(A$^3$)$_3$ (Formula XIV)

Irganox 1010 antioxidant (0.6 parts) and dibutyltin dilaurate (0.06 parts) were added to 227.5 parts of the isocyanurate of hexamethylene diisocyanate and maintained at a temperature of about 50° C. PETA (3360 parts) was added and the reaction was stirred while being kept at about 50° C. by an oil bath. After about 4 hours no residual isocyanate could be detected by IR spectroscopy.

EXAMPLE 7

Synthesis of IPDIT(MA$^1$)$_3$ (Formula XV)

To 130 parts of HEMA in a reaction vessel fitted with an air-driven stirrer were added 0.5 parts of Irganox 1010 antioxidant. The flask was heated gently to dissolve the solids. 250 Parts of powdered isocyanurate of isophorone diisocyanate having an isocyanate number of 250 (T-1890, Huls) were added to the reaction vessel in small portions with stirring, so that the temperature of reaction remained below 70° C. After four hours, 88.2 parts of TEGDMA were added and the reaction mixture allowed to stir for a further period of about one hour until IR spectroscopy indicated no residual isocyanate was present. The product exhibited peaks at 1535, 1630, 1710 and 3350 cm$^{-1}$. The IPDIT(MA$^1$)$_3$ resin thus prepared contained 39% TEGDMA.

EXAMPLE 8

Synthesis of IPDIT(MA$^1$)$_2$(MA$^2$)$_1$ (Formula XVI)

50 Parts of powdered isocyanurate of isophorone diisocyanate were placed in a reaction vessel equipped with an air driven stirring assembly and thermometer. To this was added five parts toluene followed by stirring until a gelatinous mixture was obtained. Into 173.2 parts of HEMA were dissolved 0.5 parts of Irganox 1010 antioxidant and 0.9 parts of dibutyltin dilaurate. The HEMA solution was then added dropwise to the reaction vessel while keeping the reaction temperature below 60° C. After the addition was complete the reaction mixture was stirred at 60° C. for one-half hour. This was followed by a dropwise addition of 152 parts GDMA containing 0.9 parts dibutyltin dilaurate. The rate of addition was controlled so that the reaction temperature remained below 60° C. After the addition of GDMA was complete the reaction was allowed to proceed at 60° C. for ten hours. Then 350 parts of TEGDMA were added and the reaction allowed to proceed for another 5 hours. Analysis by IR spectroscopy showed that no residual isocyanate could be detected, and showed representative peaks at 1535, 1630, 1710 and 3350 cm$^{-1}$.

EXAMPLE 9

Synthesis of TDIT(MA$^1$)$_3$ (Formula XVII)

A 5% solution of choline base was prepared by diluting 45% choline base solution in methanol (Sigma Chemical Co., St. Louis, Mo.) with an 8:1 1-octanol:1-methanol mixture. To 500 parts of toluene diisocyanate in a reaction vessel mounted in an ice bath and equipped with a reflux condenser, stirrer and nitrogen bubbler, were added eight parts of the 5% choline base solution. A vigorous, exothermic reaction occurred. A white crystalline solid appeared after approximately 10 minutes of stirring. After cooling to room temperature the white solid was analyzed by IR spectroscopy. On the basis of its IR absorption bands at 2350, 1710 and 1600 cm$^{-1}$, the product was determined to be tris-(isocyanatotolyl)isocyanurate.

To a resin kettle equipped with an air-driven stirrer were added 393 parts HEMA, 0.9 parts dibutyltin dilaurate, 0.6 parts BHT and 91.5 parts TEGDMA. Powdered tris(isocyanatotolyl)isocyanurate (522 parts), prepared as above, was added in small portions while the temperature of the reaction mixture was maintained at 55°-60° C. in an oil bath. The reaction mixture was then heated at 60° C. with stirring for about 10 hours until no further isocyanate could be detected by IR spectroscopy. The product exhibited representative peaks at 1535 and 1630 cm$^{-1}$. The reaction was then stopped. IR analysis of the resulting mixture showed that it contained 50% by weight tris[(methacryloylcarbamyl)-aryl]-1,3,5-triazine,2,4,6-(1H,3H,5H)-trione ("TDI(-MA$^1$)$_3$") and 50% TEGDMA.

EXAMPLES 10–16

Various polymerizable carbamoyl isocyanurates were diluted with either TEGDMA or a mixture of TEGDMA and EBDMA to form mixtures with viscosities of 500–1000 cps. The resulting mixtures were then combined with 0.5% camphorquinone and 0.5% dimethylaminophenethanol by roll-milling.

These mixtures were then made into pastes by stirring with finely ground quartz filler which had previously been treated with gamma-methacryloxy-n-propyltrimethoxy silane. The amount of quartz filler (including the weight of silane) in the pastes varied from 82 to 86%. The pastes were placed in Teflon molds having a 7 mm diameter×2.5 mm deep cylindrical hole through the center. A piece of 2 mil polyester was placed on the top and bottom of the mold to exclude air. The pastes were then irradiated for 20 seconds with a standard dental curing light source. Barcol hardness evaluation of the top (exposed) and bottom surfaces of the samples was performed using an indenter available commercially from the Barber Colman Co., yielding hardness values on the "B" scale. Refractive index was determined under an optical microscope by comparison to standard oils of known refractive index. Water absorption was determined according to ADA specification No. 27.

For diametral tensile strength measurements, uncured paste samples were packed into a glass tube having a 4 mm inner diameter. Each sample was subjected to 40 psi pressure for 5 minutes then cured by exposure to a standard dental curing light. The cured paste was cut on a diamond saw to form a 2 mm long cylindrical plug. The plug was stored in distilled water at 37° C. for 24 hours and its diametral tensile strength then determined according to American Dental Association ("ADA") specification No. 27 using an "Instron" tensile tester.

The compressive strength was measured on samples similarly prepared, although cut to a length of 8 mm according to ADA. specification No. 9. Results of both diametral tensile and compressive strength are expressed in units of megapascals (Mpa) where 1 Mpa=10 kg/cm$^2$.

Set out below in Table II are the composition of the resin mixture (expressed in terms of the polymerizable carbamoyl isocyanurate employed, together with the weight percent diluent present), loading level, diametral tensile strength, compressive strength, and Barcol hardness for each example. Set out below in Table III are the refractive index of the resin and water absorption for each filled and cured sample. Comparison values for Bis-GMA are included in Table II.

TABLE II

| Example | Composition | Loading Level (wt %) | Diametral tensile strength (Mpa) | Compressive strength (Mpa) | Barcol hardness (top/bottom) |
|---|---|---|---|---|---|
| 10 | Formula IX + 40% TEGDMA | 85.0 | 90 | 410 | 83/81 |
| 11 | Formula IX + 23% TEGDMA 23% EBDMA | 85.0 | 93 | 432 | 82/80 |
| 12 | Formula XI + 40% TEGDMA | 85.6 | 94 | 458 | 84/84 |
| 13 | Formula XI + 23% TEGDMA 23% EBDMA | 85.0 | 96 | 469 | 84/84 |
| 14 | Formula XV + | 85.0 | 75 | 410 | 78/78 |

TABLE II-continued

| Example | Composition | Loading Level (wt %) | Diametral tensile strength (Mpa) | Compressive strength (Mpa) | Barcol hardness (top/bottom) |
|---|---|---|---|---|---|
| 15 | 50% TEGDMA Formula XVI + 50% TEGDMA | 86.0 | 77 | 424 | 80/78 |
| 16 | Formula XVII + 50% TEGDMA | 82.3 | 68 | 387 | — |
| — | BIS-GMA | — | 35–55 | 210–290 | — |

Table II shows that the polymerizable carbamoyl isocyanurates of the invention, when made into composites using a conventional filler, exhibit outstanding strength values. In comparison, conventional Bis-GMA composites result in generally lower strength values. (Reference: Restorative Dental Materials, ed. R. G. Craig, The C. V. Mosby Co., 1980, p. 398, Table 15-4).

TABLE III

| Example | Refractive index | Water absorption mg/cm$^2$ |
|---|---|---|
| 12 | 1.516 | 0.699 |
| 13 | 1.530 | 0.518 |
| 14 | 1.524 | 0.491 |
| 15 | 1.524 | 0.544 |
| 16 | 1.558 | — |

Table III shows that the dental materials of the invention have low water absorption. Table III also shows that the refractive indicies of the resins can be modified by altering the type and amount of polymerizable carbamoyl isocyanurate and diluent, thereby enabling close matching of the refractive indicies of the resin with various fillers.

EXAMPLES 17–21

Dental composites were prepared with several different fillers. The following ingredients were combined:

| Ingredients | Amount Weight Percent |
|---|---|
| Formula XII | 42.5% |
| Pentaerythritol tetramethacrylate | 2.5% |
| TEGDMA | 33% |
| EBDMA | 22% |
| | 100% |

In example 19, 33% of an oligomer of a $C_{12}$ hydrocarbon diol (Chemlink 2000, Sartomer Co.) was used in place of TEGDMA.

To the above ingredients were added 0.5% camphorquinone and 0.5% dimethylaminophenethanol. The resulting mixtures were made into pastes by hand-spatulating with a filler. Filler A was a 5.5:1 mole ratio $SiO_2:ZrO_2$ filler prepared from filtered sols according to the method of U.S Pat. No. 4,503,169 and containing 20% "OX-50" submicron silica. Filler B was finely ground quartz. The pastes were evaluated as described above. Set out below in Table IV are the loading level, diametral tensile strength, compressive strength, and Barcol hardness for each example.

TABLE IV

| Example | Filler | Loading level (wt %) | Diametral tensile strength (Mpa) | Compressive strength (Mpa) | Barcol hardness (top/bottom) |
|---|---|---|---|---|---|
| 17 | A | 88.0 | 110 | 485 | — |
| 18 | A | 86.7 | 112 | 488 | 84/82 |
| 19 | A | 87.0 | 112 | 478 | 83/81 |
| 20 | B | 86.0 | 75 | 399 | 73/67 |
| 21 | B | 86.0 | 87 | 428 | — |

Table IV shows that with filler A it is possible to obtain more highly loaded composites and higher diametral tensile strengths and compressive strength than with standard quartz filler.

EXAMPLE 22

Several unfilled dental materials were prepared as a plug, cured and evaluated for Barcol hardness as described in Examples 10–15. Set forth below in Table V are the composition and respective hardness values for each dental material.

TABLE V

| Polymerizable Carbamoyl Isocyanurate | Barcol hardness (top/bottom) |
|---|---|
| Formula VII | 52/51 |
| Formula XI | 52/51 |
| Formula XII + 50% TEGDMA | 40/38 |
| Formula XII + 23% EBDMA, 23% TEGDMA | 44/44 |
| Formula XIII | 61/57 |
| Formula XIV | 57/55 |
| Formula XV + 50% TEGDMA | 51/50 |
| Formula XVI + 50% TEGDMA | 40/38 |
| Bis-GMA + 26% TEGDMA | 42/42 |
| Bis-GMA + 50% TEGDMA | 49/48 |

This example shows that the unfilled dental material of the invention can exhibit hardness values comparable to or higher than those obtained with unfilled samples based on Bis-GMA.

EXAMPLE 23

The cytotoxicity of a cured dental material containing the polymerizable carbamoyl isocyanurate of Formula XII with 20% TEGDMA was determined by an agar overlay method similar to that described by Guess et al., J. Pharm. Sci., 54:156 (1965). The results of this test indicated that the dental material was acceptable for dental applications.

EXAMPLE 24

Long-term aging studies were carried out to determine the storage stability of various pastes containing polymerizable carbamoyl isocyanurates. Pastes stored at 45° C. were evaluated periodically for premature polymerization, and pastes stored at 4° C. were evaluated periodically for the separation of phases. After 16 weeks, neither premature polymerization nor separation of phases occurred in pastes containing the mixture of ingredients used in Examples 17–19 at loading levels of 87.5% and 89.0% of filler A.

EXAMPLE 25

Cured plugs of the composite of Example 19 were analyzed for long-term hydrolytic stability in a 37° C. water bath. After 9 months, there was no significant decrease in either compressive or diametral tensile strength of these plugs as compared with values obtained before immersion.

EXAMPLE 26

The composites of Examples 17 and 18 were sent to the Forsyth Dental Center in Boston, Mass. and placed in molars of *Mucacca Fasicularis* monkeys for an extended clinical study. The composites had a very desirable consitency in their uncured state. They handled well, were easy to contour and seemed smoother than conventional dental materials. When cured, the composites could be finished rapidly and matched the tooth color well.

Various modifications and alterations will be apparent to those skilled in the art without departing from the scope and spirit of this invention, and it should be understood that this invention is not to be unduly limited to the illustrative embodiments set forth herein.

What is claimed is:

1. A method of dental treatment which comprises placing in temporary or permanent bonded or touching contact with a tooth a dental material comprising a polymerized or unpolymerized poly(ethylenically unsaturated) carbamoyl isocyanurate.

2. A method according to claim 1 wherein said dental material is a restorative or sealant which is polymerized after it contacts said tooth.

3. A method according to claim 1 wherein said dental material is a prosthesis which is shaped and polymerized before it contacts said tooth.

4. A method according to claim 1 wherein said dental material further comprises diluent monomer in admixture with said isocyanurate, said admixture having a refractive index which enables the approximation of the appearance of natural dentition.

5. A method according to claim 1 wherein said isocyanurate is an isocyanuric acid ring joined at at least one of its nitrogen atoms, by at least one radical containing a carbamoyl linkage, to at least one ethylenically unsaturated group, with at least one other ethylenically unsaturated group being joined to the same or another said radical, or to another nitrogen atom of said ring.

6. A method according to claim 1 wherein said isocyanurate has the formula

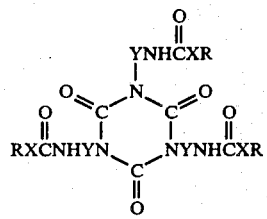

wherein each X independently is O, S, or NH, each Y independently is a non-interfering polyvalent organic linking group, and each R independently is an organic group with the proviso that at least two polymerizable ethylenically unsaturated groups are present within the R groups as a whole.

7. A method according to claim 6 wherein X is O, each Y independently is selected from the group consisting of alkylene, oxyalkylene, cycloalkylene, arylene or aralkylene groups, and each R independently is selected from the group consisting of alkylmono- or alkylpoly(acrylates and methacrylates), and mixtures thereof.

8. A method according to claim 1 wherein said isocyanurate is the reaction product of
   (a) a triisocyanato isocyanurate, and
   (b) an isocyanate-reactive compound containing at least one polymerizable ethylenically unsaturated group of the formula

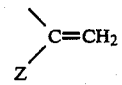

wherein Z is hydrogen, halogen or alkyl with the proviso that at least two of said ethylenically unsaturated groups are present within said reaction product.

9. A method according to claim 1 wherein said dental material further comprises filler and diluent monomer.

10. A method according to claim 9 wherein said filler is organic or inorganic filler or a combination thereof present at more than about 40% by weight of said dental material.

11. A method according to claim 9 wherein said filler is selected from the group consisting of quartz, submicron silica and non-vitreous microparticles, and said diluent monomer is selected from the group consisting of triethyleneglycol dimethacrylate and ethoxylated bisphenol A dimethacrylate and mixtures thereof.

12. A method according to claim 1 wherein said dental material comprises a mixture of:
   (a) poly(ethylenically unsaturated carbamoyl isocyanurate of the formula

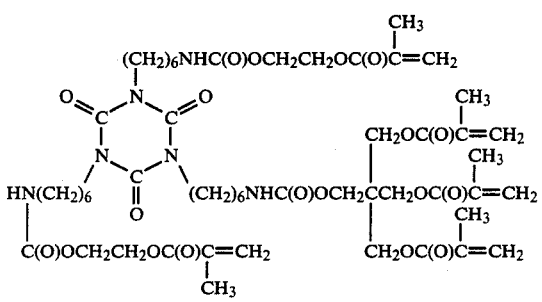

(b) filler,
(c) diluent monomer, and
(d) polymerization initiator.

13. A dental material comprising a mixture of poly(ethylenically unsaturated) carbamoyl isocyanurate and filler, said dental material being placed in temporary or permanent bonded or touching contact with a tooth.

14. A dental material according to claim 13, wherein said dental material is a restorative or sealant which is cured after it contacts said tooth.

15. A dental material according to claim 13 wherein said dental material is a prosthetic device which is shaped and cured before it contacts said tooth.

16. A tooth having in temporary or permanent bonded contact therewith a dental material comprising poly(ethylenically unsaturated) carbamoyl isocyanurate.

* * * * *